United States Patent [19]

Reeves

[11] Patent Number: 5,222,970

[45] Date of Patent: Jun. 29, 1993

[54] METHOD OF AND SYSTEM FOR MOUNTING A VASCULAR OCCLUSION BALLOON ON A DELIVERY CATHETER

[75] Inventor: Geoffrey M. Reeves, Queensland, Australia

[73] Assignee: William A. Cook Australia Pty. Ltd., Brisbane, Australia

[21] Appl. No.: 756,314

[22] Filed: Sep. 6, 1991

[51] Int. Cl.5 .................... A61M 25/00; A61M 29/02
[52] U.S. Cl. ........................................ 606/195; 604/96
[58] Field of Search ............... 606/191, 192, 194, 195; 604/96–101, 161, 160

[56] References Cited

U.S. PATENT DOCUMENTS

| Re. 31,855 | 3/1985 | Osborne | 604/161 |
|---|---|---|---|
| 3,834,394 | 9/1974 | Hunter et al. | 606/195 |
| 4,327,734 | 5/1982 | White, Jr. | 606/195 |
| 4,395,806 | 8/1983 | Wonder et al. | 29/157.1 A |
| 4,545,367 | 10/1985 | Tucci | 128/1 R |
| 4,819,637 | 4/1989 | Dormandy, Jr. et al. | 128/325 |
| 5,002,556 | 3/1991 | Ishida et al. | 604/96 |

*Primary Examiner*—C. Fred Rosenbaum
*Assistant Examiner*—William Lewis
*Attorney, Agent, or Firm*—Richard J. Godlewski

[57] ABSTRACT

A method of and system for mounting a vascular occlusion balloon on a delivery catheter. The occlusion balloon has an interior and a neck having access to the interior and a self-sealing internal balloon valve positioned at least partially in the neck. The mounting system includes a stylet having a distal end that is insertable through the longitudinal passageway of a peel-away sheath and through the internal balloon valve and into the interior of the occlusion balloon. When the stylet is inserted in the occlusion balloon, the peel-away sheath is advanced through the valve into the interior of the balloon. The stylet is removed from the balloon and peel-away sheath, and a soft durometer, flexible tip delivery catheter inserted into the interior of the balloon through the peel-away sheath. The sheath is peeled away from the delivery catheter and out of the internal balloon valve and the interior of the balloon. The mounted balloon is introduced into the vascular system through an introducer catheter and flow directed from the introducer catheter to an occlusion site. When positioned at the occlusion site, the delivery catheter inflates the occlusion balloon for lodgement in the vessel. The delivery catheter is pulled for detachment from the lodged occlusion balloon.

19 Claims, 3 Drawing Sheets

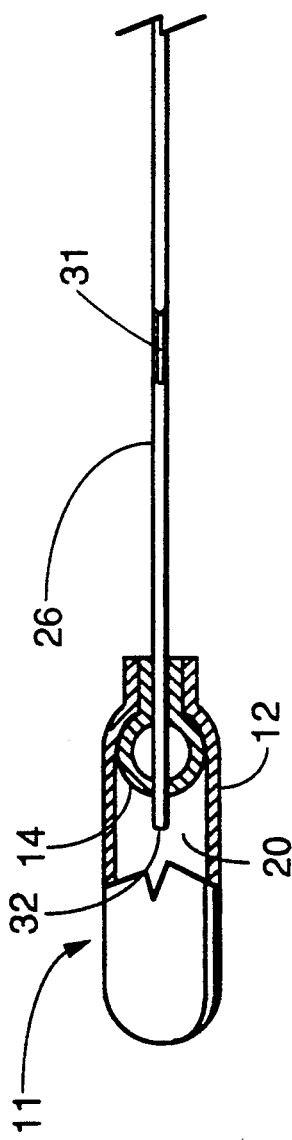
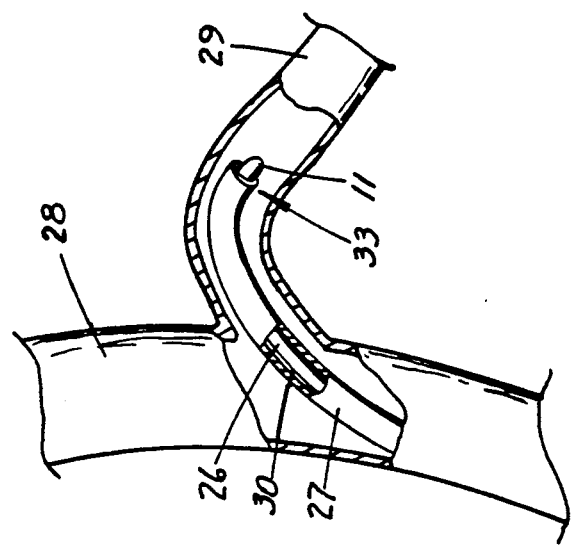
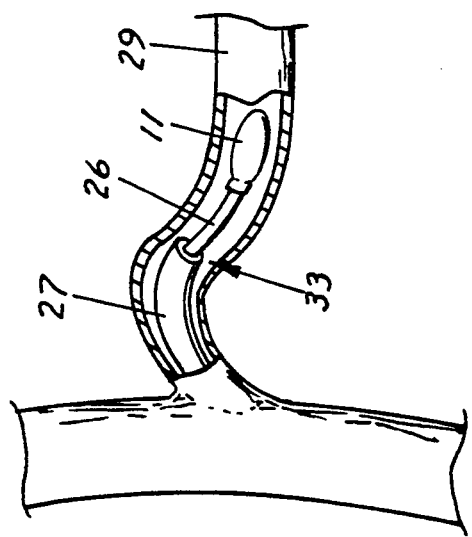
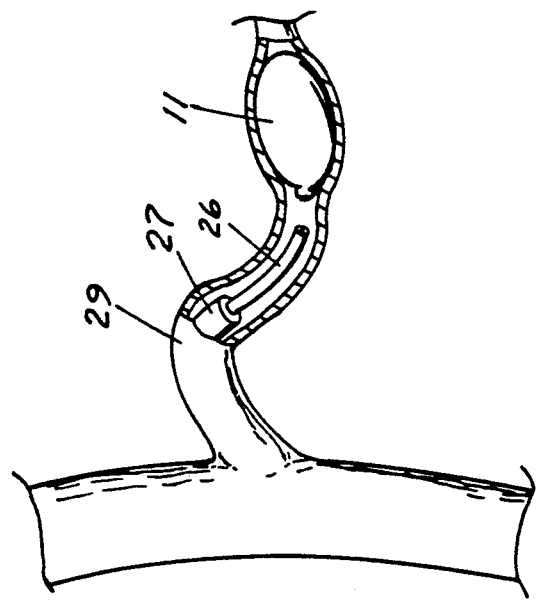

METHOD OF AND SYSTEM FOR MOUNTING A VASCULAR OCCLUSION BALLOON ON A DELIVERY CATHETER

TECHNICAL FIELD

This invention relates to occlusion balloons and delivery catheters and, in particular, to a method of and system for mounting an occlusion balloon on a soft durometer, flexible tip delivery catheter.

BACKGROUND OF THE INVENTION

Various detachable balloon systems are used for vascular occlusion procedures to treat, for example, sacular aneurysms and sinus fistulas during therapeutic embolization of a peripheral or cerebral blood vessel. A detachable balloon is typically attached to a fluid delivery catheter, inserted through an introducer catheter that is positioned proximal an occlusion site, flow-directed to the occlusion site, and inflated to an expanded state. As the fluid delivery catheter is removed from the inflated balloon, the balloon is sealed closed. To navigate through small, tortuous vessels to an occlusion site, a soft durometer, flexible delivery catheter is required. However, mounting a balloon onto a soft durometer, flexible delivery catheter without premature detachment in the vascular system is problematic.

Occlusion balloon valves are available to admit a soft durometer, flexible delivery catheter therethrough and into the interior of the occlusion balloon without damaging or deforming the delivery catheter. However, the resulting detachment force between the balloon valve and delivery catheter is so low as to establish a high probability of premature detachment in the vascular system. When premature detachment occurs, the balloon moves freely through the vascular system to cause an artificial embolization at an undesirable site, resulting in a possible stroke, heart attack, pulmonary embolism, hemorrhage, or other tissue damage. To increase the detachment force, several unsatisfactory solutions have been suggested. One prior art solution increases the detachment force by increasing the durometer of the delivery catheter to prevent damage and deformation thereof when inserted through and friction-fitted in the balloon valve. However, this higher durometer delivery catheter is unable to navigate smaller, tortuous vessels.

Other prior art solutions include increasing the length of the valve to increase the contact surface area between the valve and delivery catheter or using a tie to close the valve after the balloon is inserted therethrough. However, the longer length valve or the tie end significantly increases the probability of forming life-threatening thrombi about the balloon. In addition, the longer length valve or tie end increases blood flow turbulence and pressure about the occlusion site. This increase in pressure is particularly undesirable in occluded or weak blood vessels such as those requiring embolization procedures. Another disadvantage of this type of balloon closure on detachable balloons is that two or more balloons cannot be positioned in close proximity to each other due to the presence of the tie or long valve extending from the balloon closure.

SUMMARY OF THE INVENTION

The foregoing problems are solved and advance is achieved in an illustrative system and method for mounting a vascular occlusion balloon on a soft durometer, flexible delivery catheter for delivery particularly through small, tortuous vessels to an occlusion site. The vascular occlusion balloon has a neck having access to the interior of the balloon and an internal, self-sealing balloon valve positioned in the neck for positioning the distal end of the delivery catheter therethrough. The delivery catheter carries the mounted balloon to the occlusion site and inflates the balloon to an expanded state, thereby establishing an artificial occlusion in a patient's vascular system. When the occlusion balloon is inflated and lodged in the vessel at the occlusion site, the delivery catheter is pulled from the self-sealing valve and removed from the vascular system. In its basic form, the mounting system includes a stylet having a distal end for insertion through the internal valve and into the interior of the vascular occlusion balloon. The mounting system also includes a peel-away sheath having a longitudinal passageway extending therethrough for insertion over the stylet through the balloon valve, and into the interior of the occlusion balloon. When the sheath is positioned in the balloon interior, the stylet is withdrawn, and the soft durometer delivery catheter is advantageously inserted therein without damaging or deforming the catheter. Advantageously, the peel-away sheath is comprised of a slick-surfaced polytetrafluoroethylene material for easy insertion of the sheath through the internal valve of the occlusion balloon.

The method of mounting the detachable, vascular occlusion balloon includes inserting the stylet through the longitudinal passageway of the peel-away sheath and inserting the distal end of the stylet through the internal valve and into the interior of the occlusion balloon. The peel-away sheath is advanced over the stylet through the internal valve and into the interior of the occlusion balloon. The stylet is removed from the passageway of the advanced peel-away sheath, and the delivery catheter is inserted through the peel-away sheath into the interior of the occlusion balloon. The sheath is peeled away from the delivery catheter and out of the interior and internal valve of the occlusion balloon.

The use of the peel-away sheath advantageously introduces small diameter, soft durometer flexible tip delivery catheters through the internal valve of the occlusion balloon while still being able to maintain desirable balloon detachment forces. Sufficiently high detachment forces prevent the premature detachment of the balloon during placement. The small diameter, soft durometer flexible tip delivery catheter is readily directed through and positioned in tortuous passageways of the vascular system. The flexible tip delivery catheter is also atraumatic to the vascular vessels. As a result, the valve of the balloon can be much shorter in length and have less "tail" because of the peel-away sheath. The resulting short neck of the valve leaves very little, if any, tail outside the balloon for minimizing the formation of thrombus. The use of the peel-away sheath permits the use of a short neck on the balloon, which represents a significant departure in the art. Two or more of these short neck balloons may be positioned in close proximity to each other. As previously indicated, long tails on embolization or occlusion balloon valves prevent close proximity placement of two or more balloons.

The mounting method further includes percutaneously introducing an introducer catheter proximal to the occlusion site and passing the occlusion balloon on the distal end of the delivery catheter through the introducer catheter. The occlusion balloon on the delivery catheter is flow-directed from the distal end of the introducer catheter to the occlusion site where the occlusion balloon is inflated to an expanded state. The inflation of the balloon is advantageously performed with a polymer material introduced into the balloon via the delivery catheter. The use of a solidifying polymer material advantageously eliminates the problem of inflating fluid leaching through the balloon wall. After inflation and lodgement of the balloon, the delivery catheter is detached from the balloon by pulling the delivery catheter from the internal balloon valve.

In another aspect, the system comprises a detachable, vascular occlusion balloon system. This system includes an occlusion balloon having a neck with access to the interior of the balloon and an internal balloon valve positioned at least partially in the neck. A peel-away sheath is also included having a passageway extending longitudinally therethrough and insertable through the internal valve and into the interior of the occlusion balloon. The system also includes a delivery catheter that is insertable through the passageway of the sheath and into the interior of the occlusion balloon. The passageway of the delivery catheter extends longitudinally therethrough for inflation of the occlusion balloon to an expanded state.

The occlusion balloon system further comprises a stylet that is insertable through the internal balloon valve and into the interior of the occlusion balloon for advancing the peel-away sheath advantageously into the interior of the occlusion balloon. The peel-away sheath advantageously allows the use of flexible tip delivery catheters comprising a polymer material such as polyethylene or nylon having a low durometer. As previously suggested, the peel-away sheath also advantageously permits the use of internal balloon valves having a passageway ranging in size from 0.0075" to 0.015" in diameter and necks much shorter in length than prior art designs.

The balloon system further comprises a liquid inflation material consisting of a solidifying polymer, contrast medium, or saline introduced through the passageway of the delivery catheter for inflating the occlusion balloon to the expanded state. Also included is an introducer catheter having a passageway extending therethrough and sized for insertion of the occlusion balloon mounted on the delivery catheter, which is then advantageously flow-directed to the occlusion site.

The balloon system in another aspect comprises the occlusion balloon with the peel-away sheath inserted in the balloon interior. This combination facilitates the mounting of the balloon on the distal end of the delivery catheter. Another aspect of the invention comprises the delivery catheter inserted in the occlusion balloon.

BRIEF DESCRIPTION OF THE DRAWING

FIG. 5 depicts the occlusion balloon of FIG. 4 with the sheath peeled away from the delivery catheter, internal balloon valve, and interior of the occlusion balloon;

FIG. 6 depicts an introducer catheter of the present invention percutaneously inserted into the vascular system with the occlusion balloon extending from the proximal end thereof into the vessel;

FIG. 7 depicts the mounted occlusion balloon of FIG. 6 being flow-directed from the proximal end of the introducer catheter to the occlusion site; and FIG. 8 depicts the occlusion balloon of FIG. 7 inflated and lodged at the occlusion site and the delivery catheter being detached therefrom.

DETAILED DESCRIPTION

Figure 1:
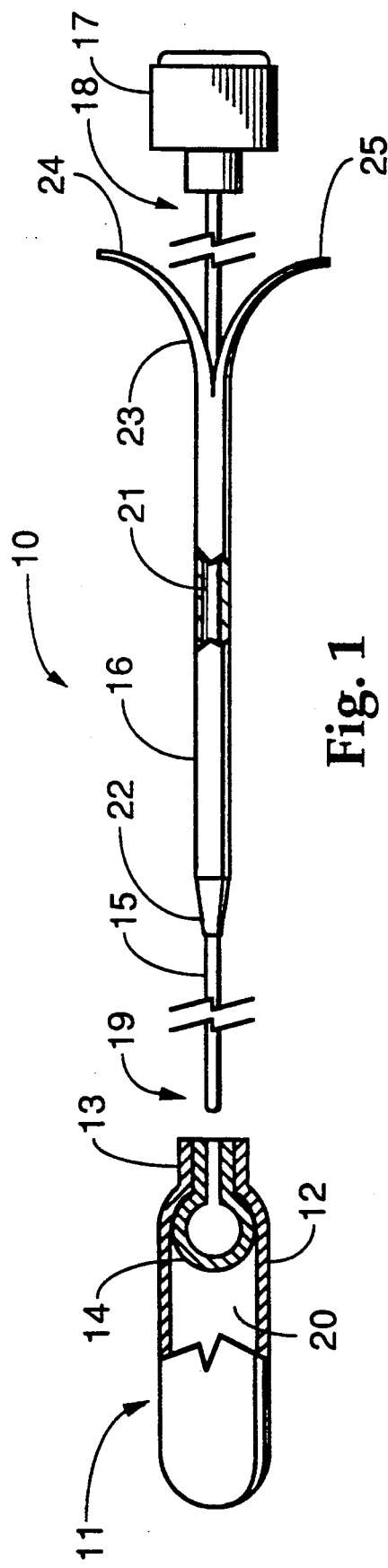
FIG. 1 depicts a preferred embodiment of a system for mounting a vascular occlusion balloon on a delivery catheter.

FIG. 1 depicts a preferred embodiment of illustrative system 10 for mounting vascular occlusion balloon 11 on a delivery catheter (not shown). The vascular occlusion balloon includes an outer detachable and inflatable balloon 12 having interior 20, neck 13 having access to the interior, and internal balloon valve 14 positioned at least partially in the neck. The mounting system includes loading stylet 15 and peel-away sheath 16. The loading stylet includes control knob 17 positioned about proximal end 18 for control of the stylet and insertion of distal end 19 through the internal balloon valve of the occlusion balloon and into interior 20 of the outer occlusion balloon. The peel-away sheath includes longitudinal passageway 21 for passage of the loading stylet therethrough. The peel-away sheath includes tapered distal end 22 for advancement over the loading stylet and insertion into the internal valve of the occlusion balloon. Proximal end 23 of the peel-away sheath is longitudinally split in half to form peel-away tabs 24 and 25. These tabs are pulled apart by the physician to peel the sheath from the delivery catheter and out of the interior and internal valve of the balloon. This peel-away sheath, which is commercially available from Cook Incorporated, Bloomington, Ind., is made from a polytetrafluoroethylene material which has a slick outer surface for easy insertion into the internal valve of the balloon.

Occlusion balloon 11, known as the COOK HAPS Emballoon, is a latex detachable balloon commercially available from William A. Cook Australia Pty. Ltd., Eight Mile Plains, Queensland, Australia. The universal size of this occlusion balloon is the R.P.H. No. 3 Emballoon, which when inflated with a 1.0 ml volume of polymer inflates the balloon to a length of 23.5 mm with an outside diameter of 7.25 mm. The uninflated length of this balloon is approximately 6.50 mm with an outside diameter of 1.32 mm. When inflated with a polymer volume of 1.5 ml, the length of the inflated balloon is 27 mm with an outside diameter of 8.50 mm. When further inflated with a polymer volume of 1.8 ml, the length of the inflated balloon is 30 mm with an outside diameter of 8.70 mm. However, the preferred inflation volume is 1.0 ml, which provides a safety factor of almost 100 percent. The average detachment pressure of the R.P.H. No. 3 Emballoon is approximately 27 grams using saline at 36 degrees Celsius. The detachment force may vary with different types of balloon filling agents. For instance, it has been observed that various agents vary the detachment force from a high of 40 grams using saline to 22 grams using a polymer. Detachment force is measured by inflating the balloon in a tube to a 1 ml volume and attaching a spring balance to the tube. The pull rate is measured on a gauge on the spring balance. Experiments were conducted as indicated at the 1.0 ml, 1.5 ml, and 1.8 ml infused volumes. Detachment pressure is also regulated by the placement of the valve in the balloon neck. The further the valve is placed through the neck, the higher the detachment pressure required. It has also been found that detachment pressures increase when the balloon is mounted on the delivery catheter for more than an hour. Experiments in dogs indicated that when the detachment pressure reaches 30 grams, it becomes difficult to detach the balloon, and the delivery catheter begins to stretch. As a result, a detachment pressure of approximately 27 grams is preferred. Internal balloon valve 14 is also a latex balloon formed utilizing a well-known dipping procedure. The valve is attached to neck 13 of the occlusion balloon with an application of latex and then trimmed to size. The occlusion balloon and the internal balloon valve may also be made of other suitable materials such as silicone. The neck of the balloon and the internal balloon valve have a passageway extending therein ranging from 0.0075" to 0.015" in diameter. Furthermore, the use of the loading stylet and peel-away sheath has reduced the length of the neck to no more than 4 mm in length.

Loading stylet 15 is a stainless steel rod approximately 7 cm in length and having a diameter of approximately 0.0175". The peel-away sheath is approximately 6.5 cm in length having an inside passageway diameter of approximately 0.0285" and an outside diameter of approximately 2.5 French. The peel-away sheath is comprised of polytetrafluoroethylene that is a lubricous material and exhibits a low coefficient of friction.

Figure 2:
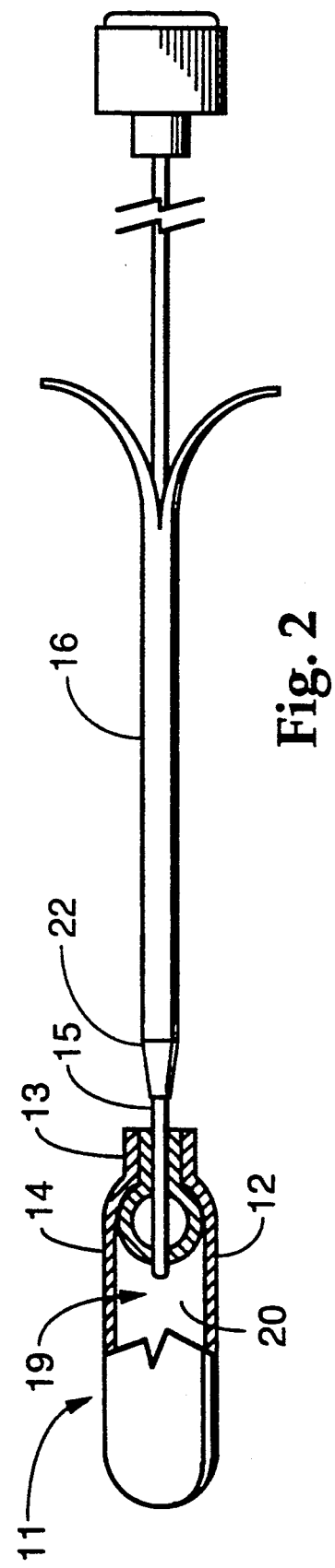
FIG. 2 depicts the loading stylet, peel-away sheath, and occlusion balloon of FIG. 1 with the loading stylet inserted through the peel-away sheath and into the interior of the occlusion balloon.

FIG. 2 depicts distal end 19 of loading stylet 15 positioned in interior 20 of outer occlusion balloon 12. The distal end of the stylet is positioned in the interior of the balloon by extension from distal end 22 of peel-away sheath 16 and passage through internal balloon valve 14.

Figure 3:
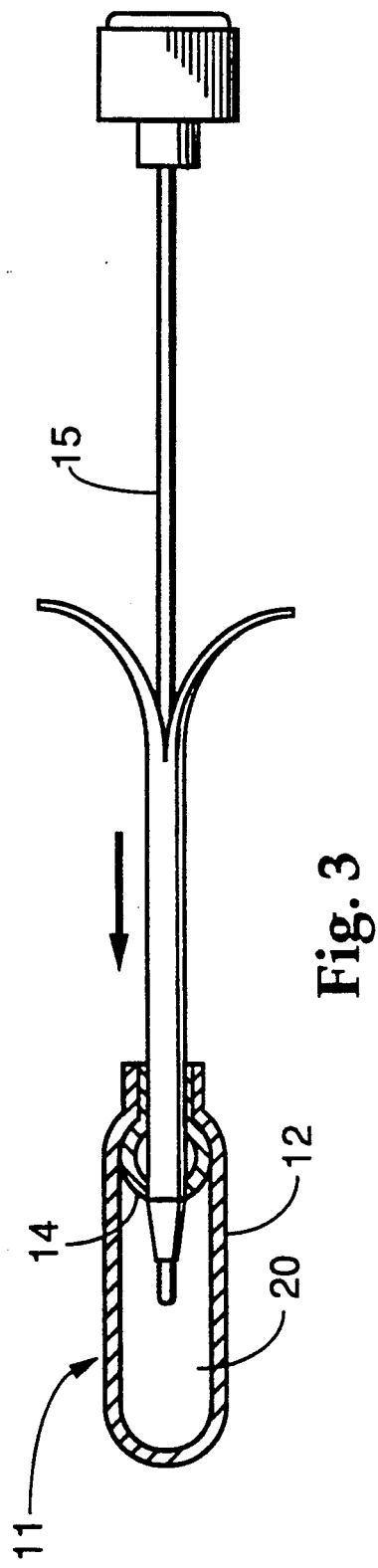
FIG. 3 depicts the mounting system of FIG. 2 with the peel-away sheath advanced over the loading stylet and into the interior of the occlusion balloon.

FIG. 3 depicts the peel-away sheath advanced over the loading stylet, through internal balloon valve 14, and into interior 20 of occlusion balloon 11. When the peel-away sheath is advanced into the interior of the occlusion balloon, the loading stylet is removed from the passageway of the sheath.

Figure 4:
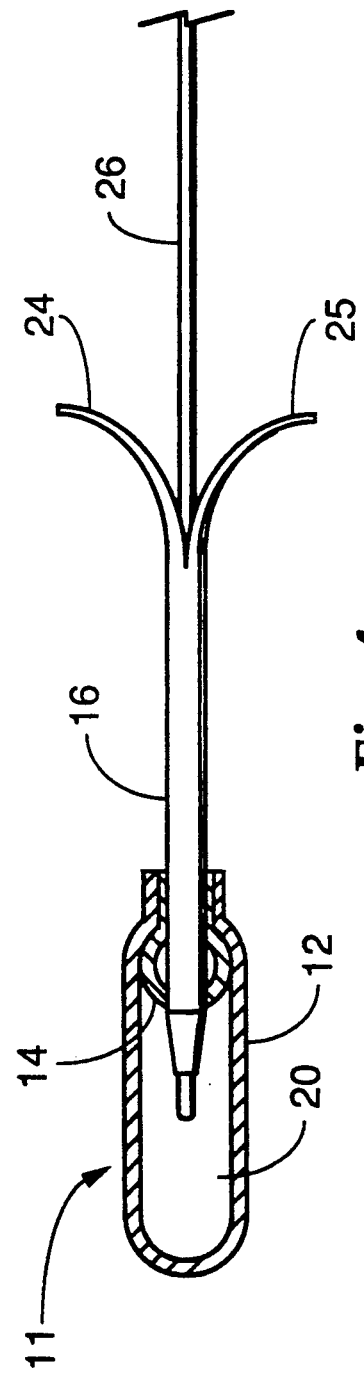
FIG. 4 depicts the mounting system and occlusion balloon of FIG. 3 with the loading stylet removed and a delivery catheter inserted through the peel-away sheath and into the interior of the occlusion balloon.

FIG. 4 depicts delivery catheter 26 inserted through the passageway of the sheath and into interior 20 of outer occlusion balloon 12. The soft, low durometer, high coefficient of friction delivery catheter moves easily and readily through the low coefficient of friction, lubricous material sheath. Tabs 24 and 25 of peel-away sheath 16 are then pulled apart, peeling the remainder of the sheath away from the delivery catheter and out of the internal balloon valve and the interior of the occlusion balloon. As is evident, the peel-away action allows the sheath to be removed from the valve with the delivery catheter remaining in place positioned through the valve. This is particularly advantageous for placing small diameter, low durometer delivery catheters in similarly low durometer internal balloon valves.

FIG. 5 depicts delivery catheter 26 firmly positioned through internal balloon valve 14 and in interior 20 of outer occlusion balloon 12. The delivery catheter is a 0.0185" outside diameter catheter approximately 140 cm in length. The delivery catheter is comprised of flexible polymer material such as polyetheline or nylon having a soft durometer believed to be in the range of 55 to 75 on the Type A International Rubber Hardness Degrees as detailed in Australian Standard AS 1683.15.1-1990 and AS 1683.15.2-1990 scale. The delivery catheter includes distal end 32 and passageway 31 extending longitudinally therethrough for introducing a liquid material such as a polymer, contrast medium, or saline into the interior of the balloon. A preferred solidifying polymer, "HEMA", is commercially available from Ubichem Limited, Eastleigh, Hampshire, England. The HEMA polymer consists of a working solution of 1 ml of Omnipaque 300, ml Ubichem 2-hydroxyetheylmethocry late (HEMA) with 2% ethylenglycoldimethacrylate (EGDM), and 0.25 ml hydrogen peroxide 3% ($H_2O_2$) added to a catalyst 0.1 ml ferrous ammonium Sulphate 50 mg/ml. On addition of the catalyst to the working solution, thickening occurs in 13 minutes at 38.4 degrees Celsius. A gel occurs in 16 minutes. A solid with a little fluid occurs in 20 minutes, whereas a solid with no fluid occurs in two and a half hours.

FIG. 6 depicts the vascular occlusion balloon system of the present invention having introducer catheter 27 that is percutaneously inserted into the vascular system of the patient for introduction of mounted occlusion balloon 11. Introducer catheter 27 includes passageway 30 extending longitudinally therethrough and is percutaneously inserted in vessels 28 and 29 of a patient's vascular system with uninflated occlusion balloon 11 extending from distal end 33 of the introducer catheter. The introducer catheter is approximately 90 cm in length having an outside diameter of approximately 0.079" and an inside diameter sized for extension of the occlusion balloon and delivery catheter therefrom. This introducer catheter comprises a nylon material and is commercially available from Cook Incorporated, Bloomington, Ind.

FIG. 7 depicts mounted occlusion balloon 11 and delivery catheter 26 being flow-directed from distal end 33 of introducer catheter 27 to the occlusion or embolization site in vessel 29. At the occlusion site, the occlusion balloon is inflated with the liquid inflation material from the group consisting of the aforementioned polymer, contrast medium, or saline introduced from the passageway of the delivery catheter.

FIG. 8 depicts occlusion balloon 11 inflated to an expanded state and lodged in vessel 29 of the vascular system. Delivery catheter 26 is then detached from the lodged balloon by pulling the catheter from self-sealing internal balloon valve.

Dog experiments with soft durometer delivery catheters indicate that detachment forces in the range of 20 to 30 grams are desirable. It was found that detachment forces in excess of 30 grams caused several soft durometer delivery catheters to stretch and break during extraction from the balloon valve. It is also known that detachment forces below 20 grams present a high probability of premature detachment during placement. A detachment force of 27 grams is preferred. However, a satisfactory solution has not been presented prior to the present invention for inserting a soft durometer, flexible delivery catheter into the interior of an occlusion balloon through the balloon valve without deforming or damaging the delivery catheter, while still maintaining a friction fit with the valve to withstand premature detachment during delivery to the occlusion site.

It is to be understood that the above-described method and system of mounting an occlusion balloon on a delivery catheter is merely an illustrative embodiment of the principles of this invention and that other mounting apparatus, mounting systems, and methods may be devised by those skilled in the art without departing from the spirit and scope of this invention. It is contemplated that various other materials may be utilized for the occlusion balloon, and as a result, delivery catheters of different durometers and materials may be utilized depending on the detachment force required. In summary, the use of the peel-away sheath with the mounting system permits the introduction of soft durometer, flexible tip delivery catheters into the interior of the balloon while still maintaining high detachment forces. This minimizes premature detachment of the balloon prior to reaching the occlusion site in the vascular system.

What is claimed is:

1. A detachable, vascular occlusion balloon system comprising:
    an occlusion balloon having an interior, a neck having access to said interior, and an internal balloon valve positioned at least partially in said neck;
    a peel-away sheath having a passageway extending longitudinally therethrough and insertable through said internal balloon valve into said interior of said occlusion balloon; and
    a delivery catheter having a distal end insertable through said valve via said passageway of said peel-away sheath and into said interior of said occlusion balloon for mounting said occlusion balloon thereon, said catheter having a passageway extending longitudinally therethrough for inflation of said occlusion balloon to an expanded state.

2. The occlusion balloon system of claim further comprising a stylet having a distal end sized for insertion through said peel-away sheath, said internal balloon valve, and into said interior of said occlusion balloon.

3. The occlusion balloon system of claim 1 wherein said peel-away sheath comprises a polytetrafluoroethylene material.

4. The occlusion balloon system of claim 1 wherein said delivery catheter comprises a polymer material having a predetermined durometer.

5. The occlusion balloon system of claim 4 wherein said polymer material is from the group consisting of polyetheline or nylon.

6. The occlusion balloon system of claim 4 wherein said polymer material comprises nylon.

7. The occlusion balloon system of claim 1 further comprising a liquid material from the group consisting of a solidifying polymer, contrast medium, or saline introduced through said passageway of said delivery catheter for inflation of said occlusion balloon to said expanded state.

8. The occlusion balloon system of claim 1 further comprising an introducer catheter having a longitudinal passageway extending therethrough and sized for insertion of said occlusion balloon and said delivery catheter therethrough.

9. System for mounting a vascular occlusion balloon on a delivery catheter, said balloon having an interior, a neck having access to said interior, and an internal balloon valve positioned at least partially in said neck, comprising:
    a stylet having a distal end for insertion through said internal balloon valve and into said interior of said vascular occlusion balloon; and
    a peel-away sheath having a longitudinal passageway extending therethrough, said passageway being sized for passage of said stylet and said delivery catheter therethrough, said sheath being sized for advancement through said internal balloon valve over said stylet and into said interior of said vascular occlusion balloon.

10. A detachable, vascular occlusion balloon system comprising:
    an occlusion balloon having an interior, a neck having access to said interior, and an internal balloon valve positioned at least partially in said neck; and
    a peel-away sheath splitable longitudinally along its entire length, having a longitudinal passageway for extending a delivery catheter therethrough, and inserted through said internal balloon valve into said interior of said occlusion balloon.

11. The balloon system of claim 10 further comprising a stylet having a distal end sized for insertion through said passageway of said peel-away sheath, said internal balloon valve, and into said interior of said occlusion balloon.

12. A method of mounting on a delivery catheter a detachable, vascular occlusion balloon having an interior, a neck having access to said interior, and an internal balloon valve positioned at least partially in said neck, comprising:
    inserting a stylet through a longitudinal passageway of a peel-away sheath;
    inserting a distal end of said stylet through said valve of said occlusion balloon and into said interior of said balloon;
    advancing said peel-away sheath over said stylet through said internal balloon valve into said interior of said balloon;
    removing said stylet from said interior of said balloon and said passageway of said peel-away sheath;
    inserting a distal end of said delivery catheter through said passageway of said peel-away sheath and into said interior of said occlusion balloon; and
    peeling said sheath away from said delivery catheter and out of said internal balloon valve and said interior of said balloon.

13. The method of claim 12 further comprising percutaneously introducing an introducer catheter proximal to a predetermined site in the vascular system of a patient's body.

14. The method of claim 13 further comprising flow directing said occlusion balloon from the distal end of said introducer catheter to said predetermined site.

15. The method of claim 14 further comprising inflating said occlusion balloon to an expanded state.

16. The method of claim 15 wherein said step of inflating includes introducing a solidifying polymer material in said interior of said occlusion balloon through said delivery catheter;

17. The method of claim 16 comprising detaching said delivery catheter from said occlusion balloon when inflated to said expanded state.

18. A method of claim 17 said step of detaching said delivery catheter from said occlusion balloon includes pulling said delivery catheter from said interior of said balloon and said internal balloon valve when said occlusion balloon is in said expanded state.

19. A method of mounting on a delivery catheter a detachable, vascular occlusion balloon having an internal balloon valve, comprising:

inserting a stylet through a longitudinal passageway of a peel-away sheath;

inserting a distal end of said stylet through said valve and into the interior of said occlusion balloon;

advancing said peel-away sheath over said stylet through said internal balloon valve and into an interior of said occlusion balloon;

removing said stylet from said passageway of said peel-away sheath;

inserting a distal end of said delivery catheter through said passageway of said peel-away sheath and into said interior of said occlusion balloon;

peeling said sheath away from said delivery catheter and out of said interior of said balloon and said internal balloon valve;

percutaneously introducing an introducer catheter proximal to a predetermined site in the vascular system of a patient's body;

passing said occlusion balloon mounted on said end of said delivery catheter through said introducer catheter;

flow directing said occlusion balloon on said delivery catheter from said introducer catheter to said predetermined site;

introducing a solidifying polymer material into said interior of said occlusion balloon through said delivery catheter and said internal valve to inflate said occlusion balloon to an expanded state; and pulling said delivery catheter from said interior of said balloon and said internal balloon valve when said occlusion balloon is in said expanded state.

* * * * *